United States Patent
Robie et al.

[11] Patent Number: 6,126,692
[45] Date of Patent: Oct. 3, 2000

[54] RETAINING MECHANISM FOR A MODULAR TIBIAL COMPONENT OF A KNEE PROSTHESIS

[75] Inventors: Bruce H. Robie, Glen Rock; Daniel E. Rosenthal, Millburn, both of N.J.; Peter Nelson Schmidt, Ithaca, N.Y.

[73] Assignee: New York Society for the Relief of the Ruptured and Crippled Maintaining the Hospital for Special Surgery, New York, N.Y.

[21] Appl. No.: 09/104,562

[22] Filed: Jun. 25, 1998

[51] Int. Cl.[7] .................................. A61F 2/38; A61F 2/28
[52] U.S. Cl. ................................................ 623/20; 623/18
[58] Field of Search ...................... 623/20, 18; 29/243.56

[56] References Cited

U.S. PATENT DOCUMENTS

| | | |
|---|---|---|
| 4,213,209 | 7/1980 | Insall et al. . |
| 4,257,129 | 3/1981 | Volz . |
| 4,298,992 | 11/1981 | Burstein et al. . |
| 4,822,362 | 4/1989 | Walker et al. . |
| 4,936,853 | 6/1990 | Fabian et al. . |
| 4,944,757 | 7/1990 | Martinez et al. . |
| 5,007,933 | 4/1991 | Sidebotham et al. . |
| 5,071,438 | 12/1991 | Jones et al. . |
| 5,137,536 | 8/1992 | Koshino . |
| 5,194,066 | 3/1993 | Van Zile . |
| 5,344,460 | 9/1994 | Turanyi et al. . |
| 5,370,699 | 12/1994 | Hood et al. . |
| 5,387,240 | 2/1995 | Pottenger et al. . |
| 5,405,395 | 4/1995 | Coates . |
| 5,458,637 | 10/1995 | Hayes . |
| 5,609,641 | 3/1997 | Johnson et al. . |
| 5,645,604 | 7/1997 | Schneider et al. ....................... 623/20 |
| 5,702,463 | 12/1997 | Pothier et al. . |

*Primary Examiner*—Mickey Yu
*Assistant Examiner*—Alvin Stewart
*Attorney, Agent, or Firm*—Darby & Darby

[57] ABSTRACT

The present invention provides a tibial prosthetic knee component. The prosthesis includes a tibial tray having a posterior rail and an anterior rail, and a tibial insert. The tibial insert has a posterior dovetailed surface matching the posterior rail in the tibial tray, and an anterior surface matching the anterior rail in the tibial tray. The posterior rail of the tibial tray and the posterior dovetailed surface of the tibial insert are curved to provide clearance for the posterior cruciate ligament. A retaining clip is provided for retaining the tibial insert in the tibial tray. The clip includes a tab which extends through the tray into the insert and a resilient holding member remains unloaded when loads are applied to the knee, reducing the likelihood of dissociation of the tray and insert.

5 Claims, 5 Drawing Sheets

FIG. 9
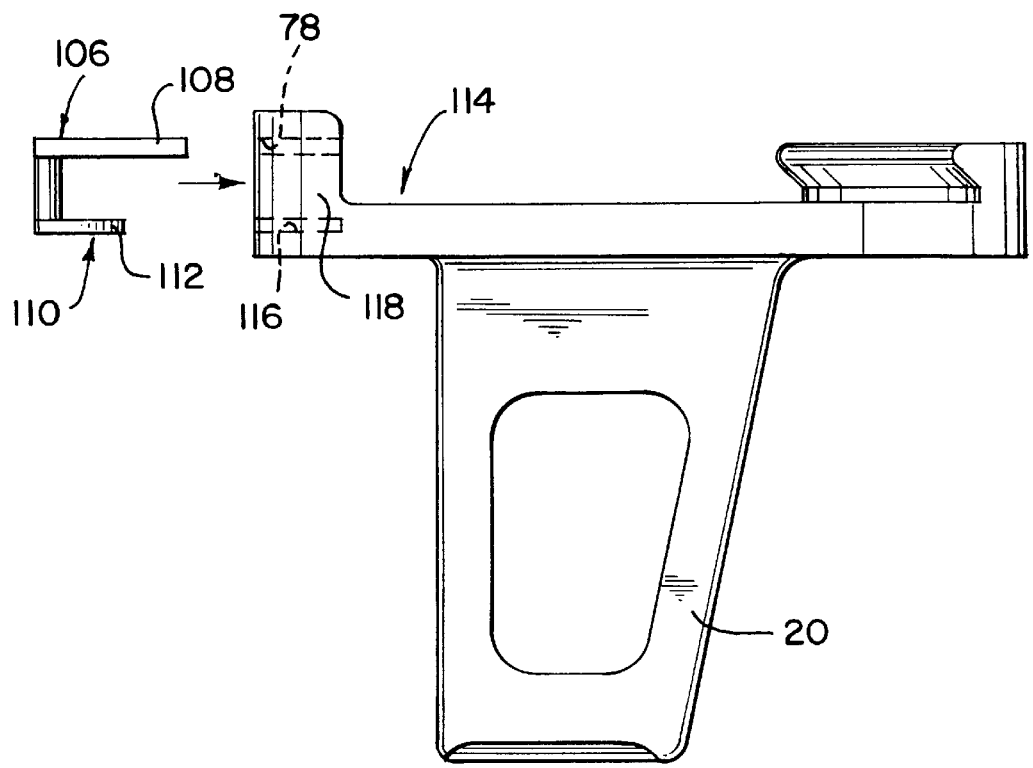
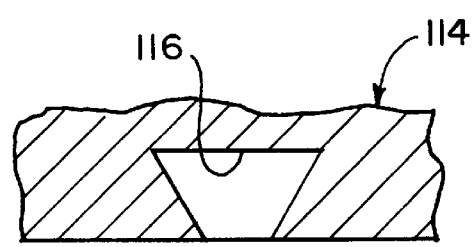
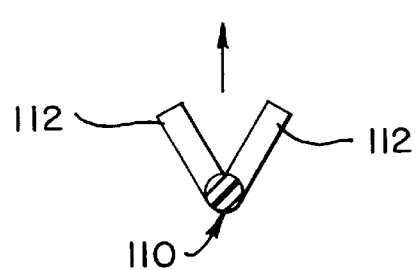
FIG. 10

RETAINING MECHANISM FOR A MODULAR TIBIAL COMPONENT OF A KNEE PROSTHESIS

BACKGROUND

1. Field of the Invention

The present invention relates generally to orthopedic prosthetic devices such as implants and artificial joints and, more particularly, to an improved retaining mechanism for the tibial component of a knee prosthesis.

2. Description of the Prior Art

The knee joint consists of the bone interface between the distal end of the femur and the proximal end of the tibia. The tibial-femoral interface is covered by the patella, a sesamoid bone within the tendon of the quadriceps on the front of the thigh. This tendon attaches to the tibial tuberosity and the posterior surface of the patella, and glides over the femur. The femur has a medial condyle and a lateral condyle which are substantially smooth and articulate with the medial condyle and lateral condyle of the tibia. The tibial condyles are slightly cupped to receive the condyles of the femur.

When the knee joint is damaged, the natural bones may be unable to articulate properly. In some cases, a prosthetic replacement of the damaged section is required to restore normal use of the joint and reduce pain. Typically the entire joint is replaced by a surgical procedure which removes the ends of the corresponding damaged bones and replaces these ends with prosthetic implants.

A total knee prosthesis includes patellar, femoral and tibial components which are intended to replace the mating surfaces of the patient's femur and tibia. The tibial component very often consists of a metal tray which is anchored in the patient's tibia and a plastic insert made of a lubricous plastic material such as ultra high molecular weight polyethylene. The plastic insert is subject to wear and, therefore, may need to be replaced with time. Replacement of the insert is simplified if it is not necessary to remove the part (tray) which is implanted in the patient's tibia. Over the years, various retaining mechanisms have been developed for holding or locking the tibial insert to the tibial tray.

U.S. Pat. No. 4,298,992 discloses a well known total knee prosthesis known as the Insall/Burstein (I-B II) posterior stabilized knee. The I-B II knee has been in use for over nine years, and in thousand of clinical cases there has been no reported dissociation of the tibial insert and tibial tray. In the commercial product, the insert is laterally loaded into the tray and captured by anterior and posterior rails, each with a dovetail, which hold the insert in place. A clip passes through the anterior rail and is held in the tray by two tines that fit in a mating recess in the tray, below the lower surface of the insert. The clip also has a protruberence that fits in a recess in the plastic to prevent medial-lateral motion of the insert relative to the tray.

Unfortunately, this retaining mechanism cannot be used in a total knee replacement where the posterior cruciate ligament (PCL) is retained because insertion of the insert would interfere with the intact posterior cruciate ligament. Current retaining mechanisms for posterior cruciate ligament retaining total knee replacements are prone to dissociation of the tibial insert because the applied loads are partially resisted by the retaining mechanism which therefore is subject to failure.

An object of the invention is to provide an improved retaining mechanism for the tibial tray of a total knee replacement, including posterior stabilized and constrained condylar knees.

Another object of the invention is to provide a retaining mechanism for the tray of the tibial component of a knee prosthesis specially adapted for use with knee replacements in which the posterior cruciate ligament is to be retained.

SUMMARY OF THE INVENTION

In accordance with the invention, the tibial component of a total knee prosthesis includes a tibial tray having upstanding anterior and posterior rails, with the posterior rail being curved to accommodate the posterior cruciate ligament. The posterior rail is dovetailed but the anterior rail is not dovetailed. A plastic tibial insert has a dovetailed posterior surface which engages the posterior rail of the tray and a nondovetailed anterior surface which engages the anterior rail of the tray. The construction is such that during assembly, the dovetail on the insert may be brought into mating engagement with the dovetail on the tray, and simultaneously rotated and slid posteriorly until the dovetail is fully engaged and the anterior surfaces are brought into mutual contact.

The insert is held in place within the tray by means of a retaining element which includes a tab which passes through the anterior rail into the insert to retain the insert in its seated position within the tray. In the preferred embodiment, the retaining element also includes a spring biased holding element which is received within an opening in the tray to hold the retaining element in position. Because the holding element is not subject to loads applied to the knee, the retaining element is not subject to displacement yet can be easily removed if it should be desirable to replace the insert.

BRIEF DESCRIPTION OF THE DRAWINGS

FIG. 9 is a left side elevational view of still another embodiment of the locking mechanism of the present invention; and FIG. 10 is a top plan sectional view of the locking mechanism of FIG. 9.

DETAILED DESCRIPTION OF THE PREFERRED EMBODIMENT

Figure 1:
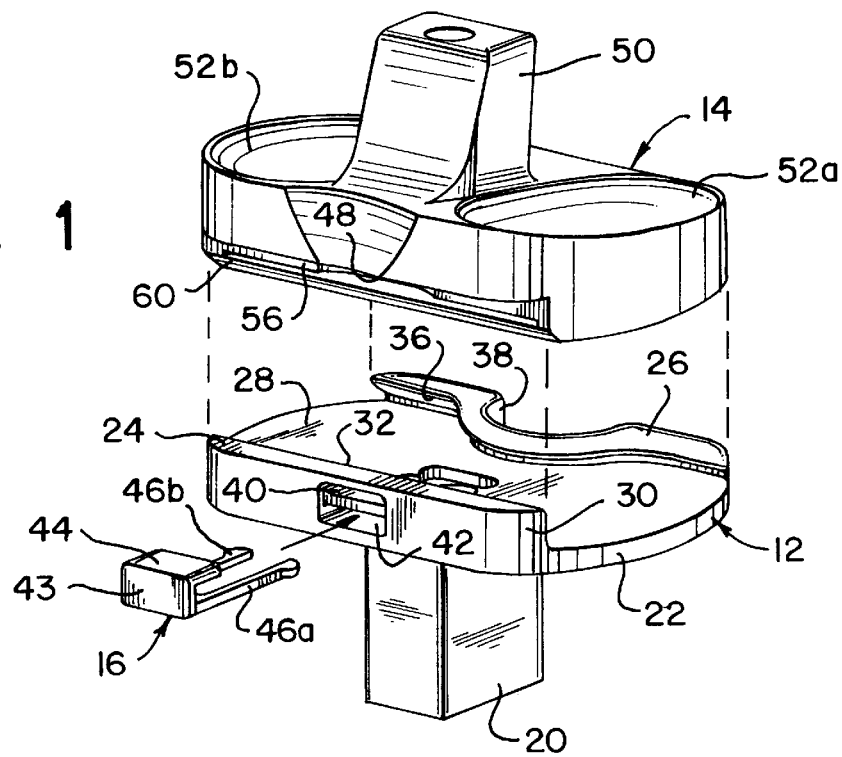
FIG. 1 is an isometric view of the tibial components of a total knee replacement and a retaining mechanism according to the invention.
Figure 2:
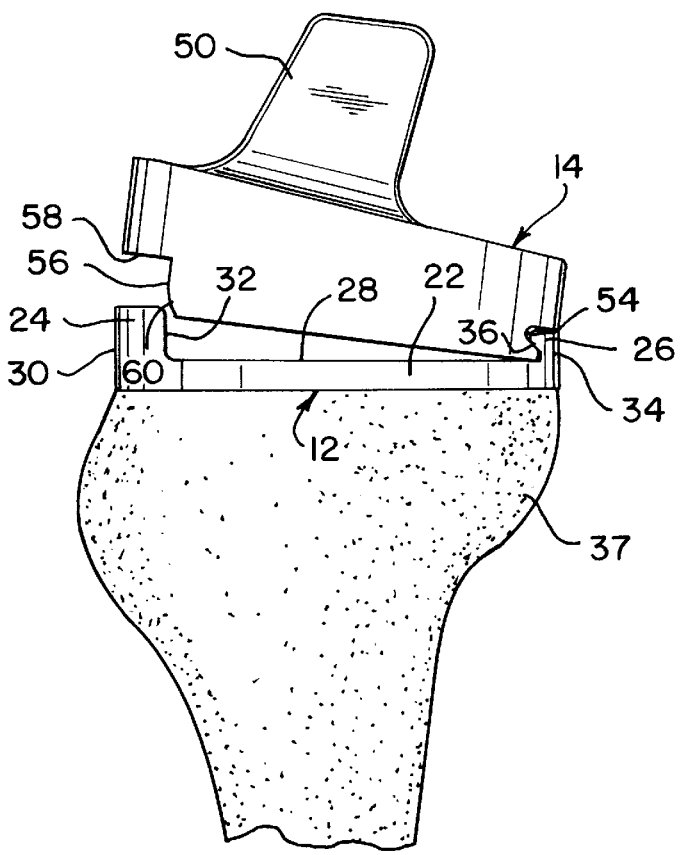
FIG. 2 is a left side elevational view of the tibial insert and tray with the insert being rotated into engagement with the tray.

FIG. 1 is an exploded view of the tibial component of a total knee prosthesis which includes a tibial tray 12, tibial insert 14 and retaining element or clip 16. The tibial tray 12 includes a fixation stem 20, a support shelf 22, and an upstanding anterior rail 24 and posterior rail 26. The support shelf 22 has a generally planar top surface 28. As shown in FIG. 2, the anterior rail 24 includes an outer wall 30 and an inner wall 32. The posterior rail 26 includes an outer wall 34 and an inner wall having a dovetailed surface 36. The inner wall 32 of the anterior wall is not dovetailed.

As used in the specification and claims, the term "dovetailed" is intended to refer to a surface(s) which is shaped so as to limit simultaneous movement of an element having a complementary engaging dovetail surface in two directions. For example, the dovetail surfaces of the insert and tray prevent removal of the insert relative to the tray in posterior (rearward) and superior (upward) directions.

The stem 20 projects downwardly from the support shelf and is inserted into the proximal tibia 37 to form a permanent connection with the tibia 37 (see FIGS. 2 and 3) in a conventional manner.

The support shelf 22 is generally oblong with a curved posterior edge where the dovetail 36 intersects the planar top surface 28. The posterior rail 26 is curved to define a clearance notch 38 for the intact posterior cruciate ligament. The top surface 28, inner wall 32 and dovetail surface 36 form a receptacle for receiving the tibial insert 14.

Figure 5:
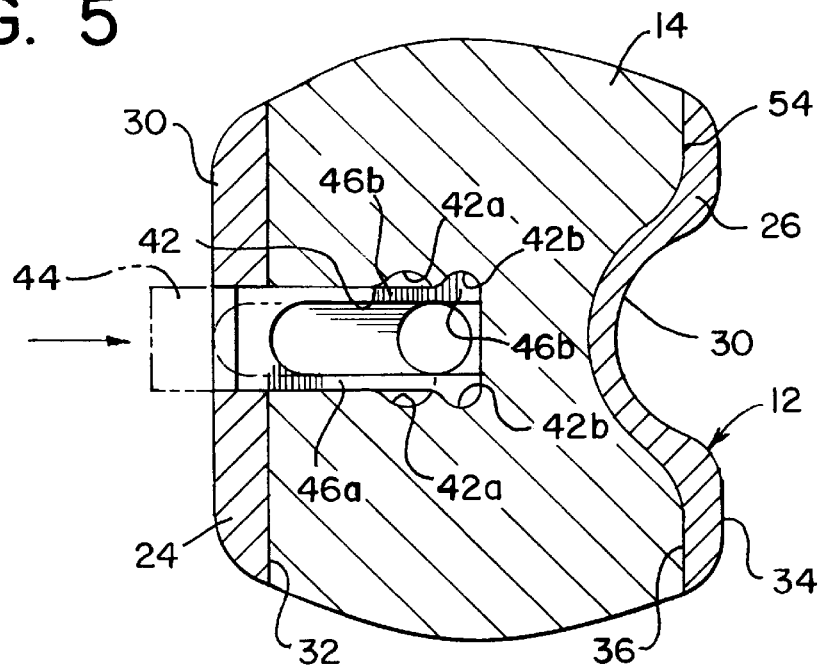
FIG. 5 is a sectional view taken along lines 5—5 in FIG. 3.
Figure 6:
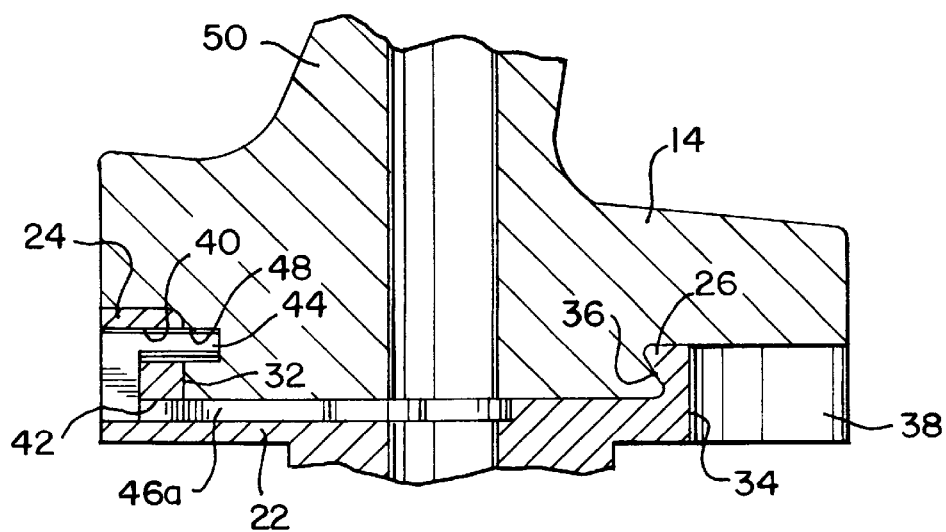
FIG. 6 is a sectional view taken along lines 6—6 in FIG. 4 showing the clip installed and the insert locked to the tray.

The retaining clip 16 includes a head portion 43, a tab 44 extending from the head portion 43, and a resilient holding member which, in one illustrative embodiment, comprises a pair of tines 46a, 46b extending from head portion 43 beneath tab 44. The anterior rail 24 includes a clip tab cutout 40 (FIG. 5) configured to receive tightly the tab 44, and a slot 42 which receives tines 46a, 46b of retaining clip 16. The clip tab cutout 40 is aligned with a corresponding cutout 48 in the tibial insert 14 (FIG. 6). The slot 42 is disposed beneath clip tab cutout 40 within the support shelf 22 and is shaped as shown in FIG. 5 to retain the tines 46a and 46b in their outwardly biased position.

The resilient engaging member 46 may take many different forms, such as a single resilient tine, a deformable rectangular insert, and the like, several of which are described in greater detail below in connection with FIGS. 7 through 10.

The tibial insert 14 is integrally formed from ultra high molecular weight polyethylene or a like material having lubricious properties. The tibial insert 14 (in the illustrated posterior stabilized embodiment) includes a stabilizing post 50, and a pair of concave depressions 52a, 52b which receive the medial and lateral condyles of the fermoral component (not shown).

The tibial insert 14 includes a posterior dovetailed surface 54 which engages dovetailed surface 36 of posterior rail 26. The posterior dovetailed surface 54 has a curved shape matching the posterior rail 26 to provide clearance for the posterior cruciate ligament as discussed above. At the opposite side, tibial insert 14 has a nondovetailed anterior surface 56 which blends into a ledge 58 and a chamfered surface 60 as shown in FIG. 2. The chamfered surface 60 allows the insert 14 to be rotated into the tray after the dovetailed posterior surfaces 36 and 54 have been engaged.

Figure 3:
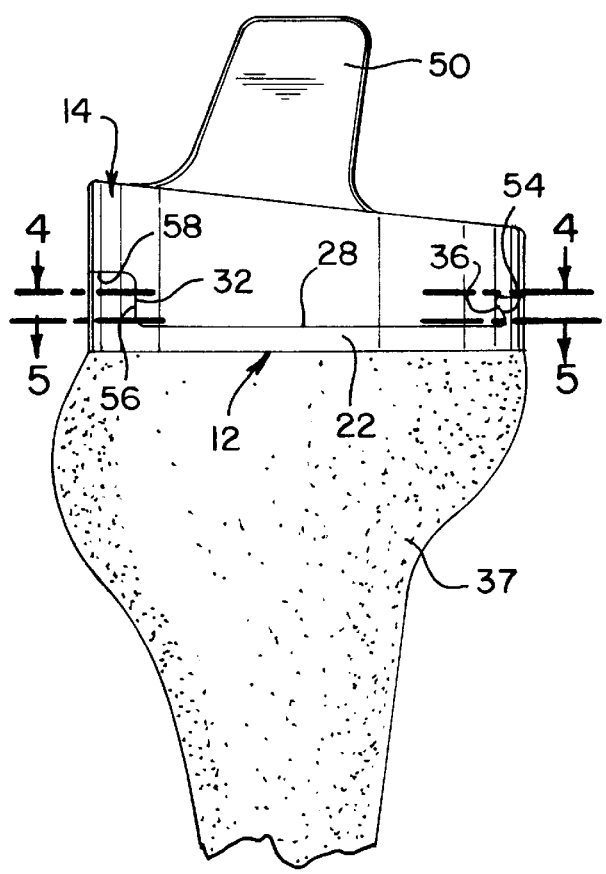
FIG. 3 is a left side elevational view of the tibial insert fully inserted into the tray.
Figure 4:
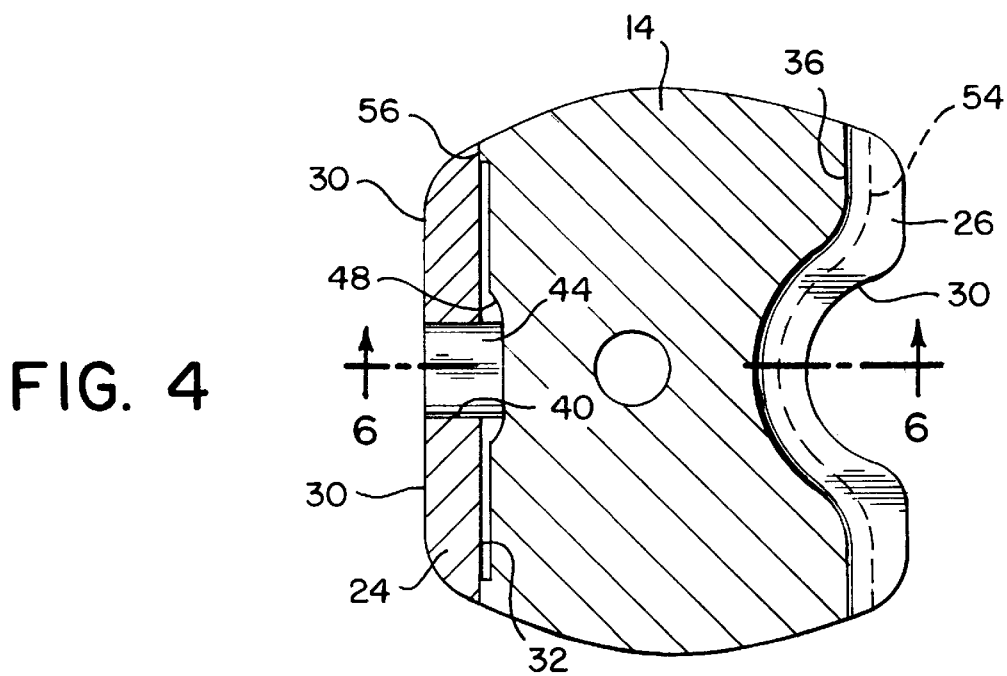
FIG. 4 is a sectional view taken along lines 4—4 in FIG. 3.

The tibial component is assembled by first engaging the corresponding dovetail surfaces 36, 54 as best seen in FIG. 2, and then rotating the insert 14 until the anterior surface 56 engages inner wall 32 of anterior rail 24 of the tibial tray 12 with the bottom surface of the insert 14 lying flat against planar surface 28 of support shelf 22 (see FIG. 3). The retaining clip 16 is then inserted through the anterior rail 24 by inserting the tab 44 through the clip tab cutout 40 and into the slot 48 in the insert, and by inserting the resilient tines 46a, 46b of the insert 46 into the slot 42. The individual parts of the tibial component may be sold in a partially assembled condition. For this purpose, the slot 42 may include notches 42a and 42b in which the protrusions at the ends of tines 46a and 46b can rest. In the partially assembled condition (shown in dotted lines in FIG. 5), the ends of the tines are received within the notches 42a. Before the prosthesis is implanted, the surgeon pushes the clip into its retention position in which the protrusions on the ends of the tines 46a and 46b rest within the notches 42b (shown in solid lines). Because the tines are retained within the tray alone, loads imparted on the assembly which tend to dissociate the insert 14 from the tibial tray 12 are only reacted to by the tab 44, which transfers the load to the anterior rail 24 via cutout 40. The load is not transferred to the tines 46a, 46b which hold the retaining clip in place. This configuration provides greater structural integrity and reduces the risk of dissociation to the prosthesis.

Figure 7:
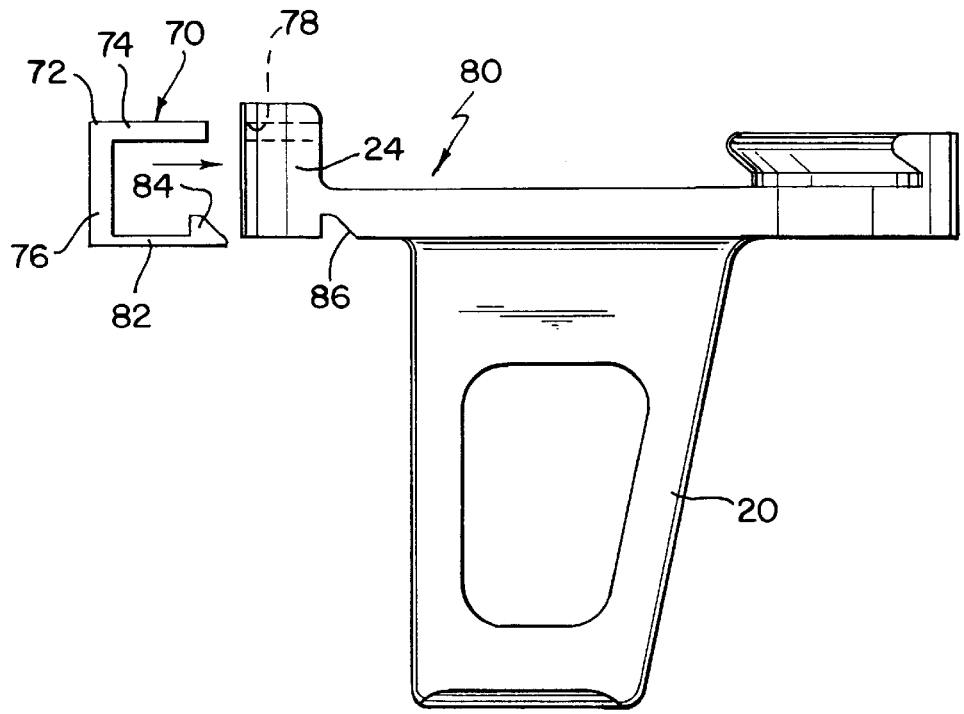
FIG. 7 is a left side elevational view of an alternate embodiment of the locking mechanism of the present invention.

Referring to FIG. 7, there is shown an alternate embodiment of the retaining element 70, which includes a clip 72 comprising a tab 74 extending from a head portion 76, the tab being configured for extension through a tab cut-out 78 formed in tray 80 and a corresponding cut-out in the tibial insert, similar to the embodiment described above. The clip further includes a holding element in the form of a deflectable finger 82 disposed beneath the tab and extending outwardly from the head portion. The finger is downwardly deflectable to clear the bottom of the anterior rail of the tray as the clip is inserted into the tray. The finger includes an upwardly projecting knob 84 at the distal end of the finger that is sized for receipt in a complementary, downwardly opening notch 86 formed on the bottom of the tray.

Figure 8:
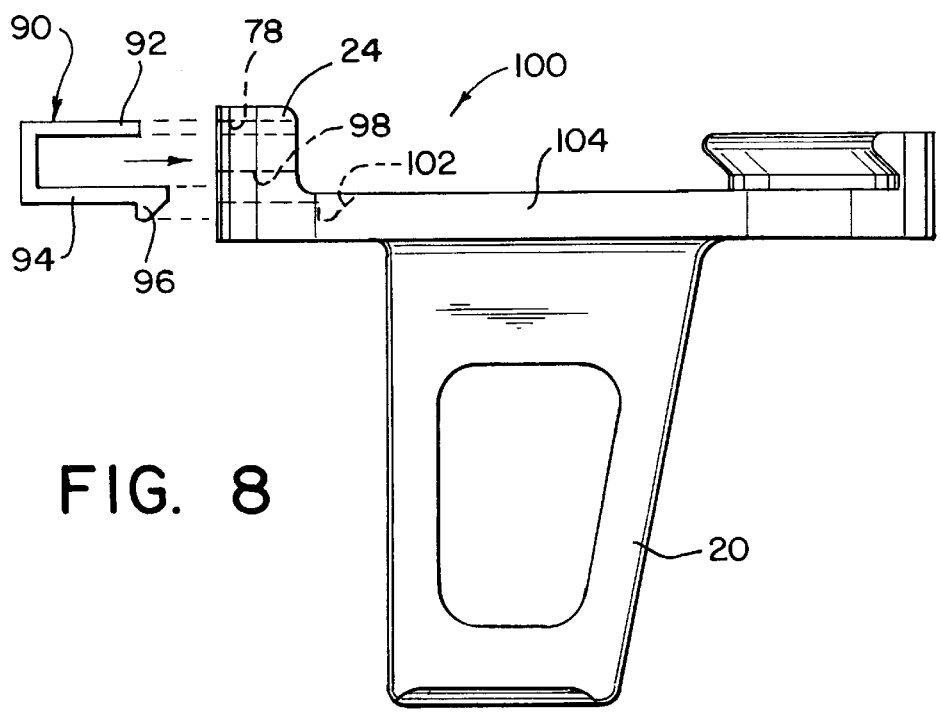
FIG. 8 is a left side elevational view of yet another alternate embodiment of the locking mechanism of the present invention.

FIG. 8 shows yet another embodiment of the retaining element, including a clip 90 comprising a tab 92 and finger 94 with a downwardly projecting knob 96 at the distal end of the finger. The finger is configured for extension through a passage 98 formed in a tray 100, with the knob received in an upwardly opening notch 102 formed in the support shelf 104 of the tray.

FIGS. 9 and 10 show still another embodiment of the retaining element. A clip 106 includes a tab 108 and a generally V-shaped holding element 110 comprising a pair of resilient fingers 112 angled outwardly from the head portion of the clip (FIG. 10). The tray 114 includes a generally trapezoidal recess 116 in the anterior rail 118 of the tray. The recess includes a relatively small opening which leads to a larger opening inside the tray body (FIG. 10). The opening is configured such that the fingers are deflected inwardly as the clip is inserted into the tray. Once the fingers are inside the recess, the fingers spread outwardly to assume their unbiased configuration, with the opening maintaining the holding element within the recess.

Thus, it will be apparent that the locking mechanism of the present invention may take many different forms and may be used with variously configured trays and inserts.

The present invention has been shown and described in what are considered to be the most practical and preferred embodiments. It is anticipated, however, that departures can be made therefrom, and that obvious modifications will be implemented by persons skilled in the art.

What is claimed is:

1. A tibial prosthetic knee component comprising:
   a tibial tray for replacing a portion of a patient's tibia, said tibial tray including a dovetailed posterior rail and an anterior rail, said tibial tray further including a clip tab cutout in said anterior rail and a support shelf;

a tibial insert having a posterior dovetail matching said posterior rail in said tibial tray, and an anterior surface matching said anterior rail in said tibial tray, said tibial insert including a cutout in said anterior surface; and a clip for locking said tibial insert to said tibial tray, said clip including a holding member and a tab spaced from the holding member, said clip retaining said tibial insert in said tibial tray when said tab is inserted through said clip tab cutout and into said cutout in said insert, and said holding member is engaged with said tray, wherein the tray includes an opening disposed beneath said clip tab cutout, and the holding member is received in said opening.

2. The tibial prosthetic knee component recited in claim 1, wherein the opening comprises a recess formed on the bottom of the tray, and the holding member comprises a deflectable finger formed with an upwardly extending knob adjacent a distal end of the finger, the knob being sized for receipt in the recess.

3. The tibial prosthetic knee component recited in claim 1, wherein the opening comprises a passage formed in the tray which leads to an upwardly opening recess, and the holding member comprises a deflectable finger having a downwardly projecting knob adjacent a distal end of the finger, the knob being sized for receipt in the recess.

4. The tibial prosthetic knee component recited in claim 1, wherein the opening comprises a generally trapezoidal recess formed in the tray, and the holding member comprises a pair of deflectable fingers in a generally V-shaped configuration and sized for receipt in the recess.

5. A tibial prosthetic knee component comprising:

a tibial tray for replacing a portion of a patient's tibia, said tibial tray including a dovetailed posterior rail and an anterior rail, said tibial tray further including a clip tab cutout in said anterior rail and a support shelf;

a tibial insert having a posterior dovetail matching said posterior rail in said tibial tray, and an anterior surface matching said anterior rail in said tibial tray, said tibial insert including a cutout in said anterior surface; and a clip for locking said tibial insert to said tibial tray, said clip including a holding member and a tab spaced from the holding member, said clip retaining said tibial insert in said tibial tray when said tab is inserted through said clip tab cutout and into said cutout in said insert, and said holding member is engaged with said tray, wherein the holding member comprises a pair of spaced apart tines.

* * * * *

UNITED STATES PATENT AND TRADEMARK OFFICE
CERTIFICATE OF CORRECTION

PATENT NO.   :   6,126,692
DATED        :   October 3, 2000
INVENTOR(S)  :   Bruce H. ROBIE et al It is certified that errors appear in the above-identified patent and that said Letters Patent is hereby corrected as shown below:

Title page, [75] Inventor, change

"ITHACA, NY" to --NEW YORK, NEW YORK--.

Signed and Sealed this

Eighth Day of May, 2001

*Attest:*

NICHOLAS P. GODICI

*Attesting Officer*     Acting Director of the United States Patent and Trademark Office